United States Patent
Chowaniec et al.

(10) Patent No.: US 9,522,002 B2
(45) Date of Patent: Dec. 20, 2016

(54) SURGICAL INSTRUMENT WITH PRESSURE DISTRIBUTION DEVICE

(71) Applicant: Covidien LP, Mansfield, MA (US)

(72) Inventors: Matthew J. Chowaniec, Middletown, CT (US); Xingrui Chen, Hamden, CT (US); Peter T. Collings, Shelton, CT (US); Luis Dussan, East Haven, CT (US); Paul D. Richard, Shelton, CT (US)

(73) Assignee: Covidien LP, Mansfield, MA (US)

( * ) Notice: Subject to any disclaimer, the term of this patent is extended or adjusted under 35 U.S.C. 154(b) by 969 days.

(21) Appl. No.: 13/713,260

(22) Filed: Dec. 13, 2012

(65) Prior Publication Data

US 2014/0166720 A1 Jun. 19, 2014

(51) Int. Cl.
*A61B 17/068* (2006.01)
*A61B 17/072* (2006.01)
*A61B 17/00* (2006.01)

(52) U.S. Cl.
CPC ....... *A61B 17/068* (2013.01); *A61B 17/07207* (2013.01); *A61B 2017/00022* (2013.01); *A61B 2017/00557* (2013.01); *A61B 2017/00862* (2013.01); *A61B 2017/00867* (2013.01); *A61B 2017/07257* (2013.01); *A61B 2017/07271* (2013.01)

(58) Field of Classification Search
CPC .................. A61B 17/07292; A61B 17/07207; A61B 2017/00867; A61B 2017/00871; A61B 2017/07271
USPC ........... 227/175.1, 176.1; 604/104, 513, 509, 604/502, 508, 107; 606/157
See application file for complete search history.

(56) References Cited

U.S. PATENT DOCUMENTS

| | | |
|---|---|---|
| 3,054,406 A | 9/1962 | Usher |
| 3,079,606 A | 3/1963 | Bobrov et al. |
| 3,124,136 A | 3/1964 | Usher |
| 3,490,675 A | 1/1970 | Green et al. |
| 3,499,591 A | 3/1970 | Green |
| 4,347,847 A | 9/1982 | Usher |
| 4,354,628 A | 10/1982 | Green |
| 4,429,695 A | 2/1984 | Green |
| 4,452,245 A | 6/1984 | Usher |
| 4,603,693 A | 8/1986 | Conta et al. |

(Continued)

FOREIGN PATENT DOCUMENTS

| | | |
|---|---|---|
| DE | 19924311 | 11/2000 |
| EP | 0577373 | 1/1994 |

(Continued)

OTHER PUBLICATIONS

Extended European Search Report corresponding to EP 15 16 6762.3 dated Jul. 16, 2015; 7 pp.

(Continued)

*Primary Examiner* — Andrew M Tecco

(57) ABSTRACT

The present disclosure is directed to a surgical apparatus, comprising an anvil jaw configured to form at least one surgical staple, a cartridge jaw configured to deploy one or more surgical staples against the anvil jaw, and a pressure distribution device attached to at least one of the anvil jaw and the cartridge jaw, wherein the pressure distribution device is configured to distribute a clamping pressure to a target tissue during a clamping and a stapling of the target tissue.

9 Claims, 6 Drawing Sheets

(56) References Cited

U.S. PATENT DOCUMENTS

| | | | |
|---|---|---|---|
| 4,605,730 A | 8/1986 | Shalaby et al. | |
| 4,655,221 A | 4/1987 | Devereux | |
| 4,834,090 A | 5/1989 | Moore | |
| 4,838,884 A | 6/1989 | Dumican et al. | |
| 4,873,977 A | 10/1989 | Avant et al. | |
| 4,930,674 A | 6/1990 | Barak | |
| 5,002,551 A | 3/1991 | Linsky et al. | |
| 5,014,899 A | 5/1991 | Presty et al. | |
| 5,040,715 A | 8/1991 | Green et al. | |
| 5,065,929 A | 11/1991 | Schulze et al. | |
| 5,156,614 A | 10/1992 | Green et al. | |
| 5,205,459 A | 4/1993 | Brinkerhoff et al. | |
| 5,254,113 A | 10/1993 | Wilk | |
| 5,263,629 A | 11/1993 | Trumbull et al. | |
| 5,314,471 A | 5/1994 | Brauker et al. | |
| 5,318,531 A | 6/1994 | Leone | |
| 5,344,454 A | 9/1994 | Clarke et al. | |
| 5,389,098 A * | 2/1995 | Tsuruta | A61B 17/00234 606/142 |
| 5,392,979 A | 2/1995 | Green et al. | |
| 5,397,324 A | 3/1995 | Carroll et al. | |
| 5,425,745 A | 6/1995 | Green et al. | |
| 5,441,193 A | 8/1995 | Gravener | |
| 5,441,507 A | 8/1995 | Wilk | |
| 5,445,644 A | 8/1995 | Pietrafitta et al. | |
| 5,465,896 A | 11/1995 | Allen et al. | |
| 5,468,253 A | 11/1995 | Bezwada et al. | |
| 5,503,638 A | 4/1996 | Cooper et al. | |
| 5,542,594 A | 8/1996 | McKean et al. | |
| 5,549,628 A | 8/1996 | Cooper et al. | |
| 5,554,119 A | 9/1996 | Harrison et al. | |
| 5,575,803 A | 11/1996 | Cooper et al. | |
| 5,611,775 A | 3/1997 | Machold et al. | |
| 5,653,756 A | 8/1997 | Clarke et al. | |
| 5,669,934 A | 9/1997 | Sawyer | |
| 5,683,809 A | 11/1997 | Freeman et al. | |
| 5,690,675 A | 11/1997 | Sawyer et al. | |
| 5,702,409 A | 12/1997 | Rayburn et al. | |
| 5,735,833 A | 4/1998 | Olson | |
| 5,749,895 A | 5/1998 | Sawyer et al. | |
| 5,752,965 A * | 5/1998 | Francis | A61B 17/07207 227/178.1 |
| 5,762,256 A | 6/1998 | Mastri et al. | |
| 5,766,188 A | 6/1998 | Igaki | |
| 5,769,892 A | 6/1998 | Kingwell | |
| 5,782,396 A | 7/1998 | Mastri et al. | |
| 5,799,857 A | 9/1998 | Robertson et al. | |
| 5,810,855 A | 9/1998 | Rayburn et al. | |
| 5,814,057 A | 9/1998 | Oi et al. | |
| 5,824,015 A | 10/1998 | Sawyer | |
| 5,833,695 A | 11/1998 | Yoon | |
| 5,843,033 A | 12/1998 | Ropiak | |
| 5,843,096 A | 12/1998 | Igaki et al. | |
| 5,866,561 A | 2/1999 | Ungs | |
| 5,895,412 A | 4/1999 | Tucker | |
| 5,902,312 A * | 5/1999 | Frater | A61B 17/07207 606/148 |
| 5,908,427 A * | 6/1999 | McKean | A61B 17/07207 606/139 |
| 5,915,616 A | 6/1999 | Viola et al. | |
| 5,931,165 A | 8/1999 | Reich et al. | |
| 5,931,847 A | 8/1999 | Bittner et al. | |
| 5,964,394 A | 10/1999 | Robertson | |
| 5,964,774 A | 10/1999 | McKean et al. | |
| 5,997,895 A | 12/1999 | Narotam et al. | |
| 6,019,791 A | 2/2000 | Wood | |
| 6,030,392 A | 2/2000 | Dakov et al. | |
| 6,032,849 A | 3/2000 | Mastri et al. | |
| 6,045,560 A | 4/2000 | McKean et al. | |
| 6,063,097 A | 5/2000 | Oi et al. | |
| 6,080,169 A | 6/2000 | Turtel | |
| 6,099,551 A | 8/2000 | Gabbay | |
| 6,149,641 A | 11/2000 | Ungs | |
| 6,149,667 A | 11/2000 | Hovland et al. | |
| 6,155,265 A | 12/2000 | Hammerslag | |
| 6,165,201 A | 12/2000 | Sawhney | |
| 6,179,862 B1 | 1/2001 | Sawhney | |
| 6,210,439 B1 | 4/2001 | Firmin et al. | |
| 6,214,020 B1 | 4/2001 | Mulhauser et al. | |
| 6,228,051 B1 | 5/2001 | Trumbull | |
| 6,241,139 B1 | 6/2001 | Milliman et al. | |
| 6,258,107 B1 | 7/2001 | Balazs et al. | |
| 6,267,772 B1 | 7/2001 | Mulhauser et al. | |
| 6,273,897 B1 | 8/2001 | Dalessandro et al. | |
| 6,280,453 B1 | 8/2001 | Kugel et al. | |
| 6,287,323 B1 | 9/2001 | Hammerslag | |
| 6,299,631 B1 | 10/2001 | Shalaby | |
| 6,312,457 B1 | 11/2001 | DiMatteo et al. | |
| 6,312,474 B1 | 11/2001 | Francis et al. | |
| 6,325,810 B1 | 12/2001 | Hamilton et al. | |
| 6,398,797 B2 | 6/2002 | Bombard et al. | |
| 6,436,030 B2 | 8/2002 | Rehil | |
| 6,451,029 B1 | 9/2002 | Yeatman | |
| 6,454,780 B1 | 9/2002 | Wallace | |
| 6,461,368 B2 | 10/2002 | Fogarty et al. | |
| 6,488,197 B1 | 12/2002 | Whitman | |
| 6,491,201 B1 | 12/2002 | Whitman | |
| 6,503,257 B2 * | 1/2003 | Grant | A61B 17/07207 606/148 |
| 6,514,283 B2 | 2/2003 | DiMatteo et al. | |
| 6,517,566 B1 | 2/2003 | Hovland et al. | |
| 6,551,356 B2 | 4/2003 | Rousseau | |
| 6,592,597 B2 | 7/2003 | Grant et al. | |
| 6,623,452 B2 | 9/2003 | Chien et al. | |
| 6,638,285 B2 | 10/2003 | Gabbay | |
| 6,652,594 B2 | 11/2003 | Francis et al. | |
| 6,656,193 B2 | 12/2003 | Grant et al. | |
| 6,669,735 B1 | 12/2003 | Pelissier | |
| 6,677,258 B2 | 1/2004 | Carroll et al. | |
| 6,681,979 B2 | 1/2004 | Whitman | |
| 6,685,714 B2 | 2/2004 | Rousseau | |
| 6,695,199 B2 | 2/2004 | Whitman | |
| 6,704,210 B1 | 3/2004 | Myers | |
| 6,723,114 B2 | 4/2004 | Shalaby | |
| 6,726,706 B2 | 4/2004 | Dominguez | |
| 6,736,823 B2 | 5/2004 | Darois et al. | |
| 6,736,854 B2 | 5/2004 | Vadurro et al. | |
| 6,746,458 B1 | 6/2004 | Cloud | |
| 6,773,458 B1 | 8/2004 | Brauker et al. | |
| 6,927,315 B1 | 8/2005 | Heinecke et al. | |
| 7,070,083 B2 * | 7/2006 | Jankowski | A61B 17/072 227/176.1 |
| 7,128,748 B2 | 10/2006 | Mooradian et al. | |
| 7,141,055 B2 | 11/2006 | Abrams et al. | |
| 7,147,138 B2 * | 12/2006 | Shelton, IV | A61B 17/07207 227/176.1 |
| 7,238,195 B2 | 7/2007 | Viola | |
| 7,311,720 B2 | 12/2007 | Mueller et al. | |
| 7,322,743 B2 | 1/2008 | Gozloo et al. | |
| 7,434,717 B2 | 10/2008 | Shelton, IV et al. | |
| 7,438,209 B1 | 10/2008 | Hess et al. | |
| 7,455,682 B2 | 11/2008 | Viola | |
| 7,547,312 B2 | 6/2009 | Bauman et al. | |
| 7,559,937 B2 | 7/2009 | de la Torre et al. | |
| 7,604,151 B2 | 10/2009 | Hess et al. | |
| 7,665,646 B2 | 2/2010 | Prommersberger | |
| 7,744,627 B2 | 6/2010 | Orban, III et al. | |
| 7,793,813 B2 | 9/2010 | Bettuchi | |
| 7,823,592 B2 * | 11/2010 | Bettuchi | A61B 17/072 128/898 |
| 7,845,533 B2 | 12/2010 | Marczyk et al. | |
| 7,845,536 B2 | 12/2010 | Viola et al. | |
| 7,909,224 B2 | 3/2011 | Prommersberger | |
| 7,922,743 B2 | 4/2011 | Heinrich et al. | |
| 8,028,883 B2 | 10/2011 | Stopek | |
| 8,113,409 B2 * | 2/2012 | Cohen | A61B 17/07207 227/175.1 |
| 8,225,981 B2 | 7/2012 | Criscuolo et al. | |
| 8,348,130 B2 * | 1/2013 | Shah | A61B 17/07207 227/179.1 |
| 8,668,129 B2 * | 3/2014 | Olson | A61B 17/072 227/175.1 |
| 2001/0007069 A1 | 7/2001 | Bombard et al. | |
| 2002/0010482 A1 | 1/2002 | Watt | |

(56) References Cited

U.S. PATENT DOCUMENTS

| | | |
|---|---|---|
| 2002/0016626 A1 | 2/2002 | DiMatteo et al. |
| 2002/0019187 A1 | 2/2002 | Carroll et al. |
| 2002/0026159 A1 | 2/2002 | Zhu et al. |
| 2002/0049454 A1 | 4/2002 | Whitman et al. |
| 2002/0052622 A1 | 5/2002 | Rousseau |
| 2002/0091397 A1 | 7/2002 | Chen |
| 2002/0133236 A1 | 9/2002 | Rousseau |
| 2002/0138152 A1 | 9/2002 | Francis et al. |
| 2002/0151911 A1 | 10/2002 | Gabbay |
| 2002/0156150 A1 | 10/2002 | Williams et al. |
| 2002/0165559 A1 | 11/2002 | Grant et al. |
| 2002/0165562 A1 | 11/2002 | Grant et al. |
| 2002/0165563 A1 | 11/2002 | Grant et al. |
| 2002/0173558 A1 | 11/2002 | Williams et al. |
| 2002/0177859 A1 | 11/2002 | Monassevitch et al. |
| 2003/0050590 A1 | 3/2003 | Kirsch |
| 2003/0065345 A1 | 4/2003 | Weadock |
| 2003/0065346 A1 | 4/2003 | Evens et al. |
| 2003/0073981 A1 | 4/2003 | Whitman et al. |
| 2003/0073982 A1 | 4/2003 | Whitman |
| 2003/0083676 A1 | 5/2003 | Wallace |
| 2003/0088256 A1 | 5/2003 | Conston et al. |
| 2003/0089757 A1 | 5/2003 | Whitman |
| 2003/0105510 A1 | 6/2003 | DiMatteo et al. |
| 2003/0111507 A1 | 6/2003 | Nunez |
| 2003/0114866 A1 | 6/2003 | Ulmsten et al. |
| 2003/0120284 A1 | 6/2003 | Palacios |
| 2003/0167064 A1 | 9/2003 | Whayne |
| 2003/0181927 A1 | 9/2003 | Wallace |
| 2003/0183671 A1 | 10/2003 | Mooradian et al. |
| 2003/0208231 A1 | 11/2003 | Williamson, IV et al. |
| 2003/0236518 A1 | 12/2003 | Marchitto et al. |
| 2004/0004105 A1* | 1/2004 | Jankowski ........... A61B 17/072 227/176.1 |
| 2004/0034377 A1 | 2/2004 | Sharkawy et al. |
| 2004/0059283 A1 | 3/2004 | Kirwan et al. |
| 2004/0092960 A1 | 5/2004 | Abrams et al. |
| 2004/0093029 A1 | 5/2004 | Zubik et al. |
| 2004/0107006 A1 | 6/2004 | Francis et al. |
| 2004/0116945 A1 | 6/2004 | Sharkawy et al. |
| 2004/0142621 A1 | 7/2004 | Carroll et al. |
| 2004/0172048 A1 | 9/2004 | Browning |
| 2004/0209059 A1 | 10/2004 | Foss |
| 2004/0215214 A1 | 10/2004 | Crews et al. |
| 2004/0215219 A1 | 10/2004 | Eldridge et al. |
| 2004/0215221 A1 | 10/2004 | Suyker et al. |
| 2004/0254590 A1 | 12/2004 | Hoffman et al. |
| 2004/0260315 A1 | 12/2004 | Dell et al. |
| 2005/0002981 A1 | 1/2005 | Lahtinen et al. |
| 2005/0021026 A1 | 1/2005 | Baily |
| 2005/0021053 A1 | 1/2005 | Heinrich |
| 2005/0021085 A1 | 1/2005 | Abrams et al. |
| 2005/0038471 A1 | 2/2005 | Chan et al. |
| 2005/0043678 A1 | 2/2005 | Freyman et al. |
| 2005/0059996 A1 | 3/2005 | Bauman et al. |
| 2005/0059997 A1 | 3/2005 | Bauman et al. |
| 2005/0070929 A1 | 3/2005 | Dalessandro et al. |
| 2005/0118435 A1 | 6/2005 | DeLucia et al. |
| 2005/0184121 A1 | 8/2005 | Heinrich |
| 2005/0228446 A1 | 10/2005 | Mooradian et al. |
| 2005/0245965 A1 | 11/2005 | Orban et al. |
| 2005/0251164 A1 | 11/2005 | Gifford, II et al. |
| 2006/0004407 A1 | 1/2006 | Hiles et al. |
| 2006/0025816 A1* | 2/2006 | Shelton, IV ..... A61B 17/07207 606/215 |
| 2006/0085032 A1 | 4/2006 | Viola |
| 2006/0085033 A1 | 4/2006 | Criscuolo et al. |
| 2006/0085034 A1 | 4/2006 | Bettuchi |
| 2006/0135992 A1 | 6/2006 | Bettuchi et al. |
| 2006/0173470 A1 | 8/2006 | Oray et al. |
| 2006/0178683 A1 | 8/2006 | Shimoji et al. |
| 2006/0212050 A1 | 9/2006 | D'Agostino et al. |
| 2006/0271104 A1 | 11/2006 | Viola et al. |
| 2007/0034669 A1 | 2/2007 | de la Torre et al. |
| 2007/0049953 A2 | 3/2007 | Shimoji et al. |
| 2007/0102472 A1* | 5/2007 | Shelton ............ A61B 17/07207 227/175.1 |
| 2007/0112361 A1* | 5/2007 | Schonholz ....... A61B 17/00234 606/151 |
| 2007/0179528 A1 | 8/2007 | Soltz et al. |
| 2007/0203509 A1 | 8/2007 | Bettuchi |
| 2007/0203510 A1 | 8/2007 | Bettuchi |
| 2007/0246505 A1 | 10/2007 | Pace-Floridia et al. |
| 2008/0029570 A1 | 2/2008 | Shelton et al. |
| 2008/0082126 A1 | 4/2008 | Murray et al. |
| 2008/0110959 A1 | 5/2008 | Orban et al. |
| 2008/0125812 A1 | 5/2008 | Zubik et al. |
| 2008/0140115 A1 | 6/2008 | Stopek |
| 2008/0161831 A1 | 7/2008 | Bauman et al. |
| 2008/0161832 A1 | 7/2008 | Bauman et al. |
| 2008/0169327 A1 | 7/2008 | Shelton et al. |
| 2008/0169328 A1 | 7/2008 | Shelton |
| 2008/0169329 A1 | 7/2008 | Shelton et al. |
| 2008/0169330 A1 | 7/2008 | Shelton et al. |
| 2008/0169331 A1 | 7/2008 | Shelton et al. |
| 2008/0169332 A1 | 7/2008 | Shelton et al. |
| 2008/0169333 A1 | 7/2008 | Shelton et al. |
| 2008/0290134 A1 | 11/2008 | Bettuchi et al. |
| 2008/0308608 A1 | 12/2008 | Prommersberger |
| 2008/0314960 A1 | 12/2008 | Marczyk et al. |
| 2009/0001121 A1 | 1/2009 | Hess et al. |
| 2009/0001122 A1 | 1/2009 | Prommersberger et al. |
| 2009/0001123 A1 | 1/2009 | Morgan et al. |
| 2009/0001124 A1 | 1/2009 | Hess et al. |
| 2009/0001125 A1 | 1/2009 | Hess et al. |
| 2009/0001126 A1 | 1/2009 | Hess et al. |
| 2009/0001128 A1 | 1/2009 | Weisenburgh, II et al. |
| 2009/0001130 A1 | 1/2009 | Hess et al. |
| 2009/0005808 A1 | 1/2009 | Hess et al. |
| 2009/0030452 A1 | 1/2009 | Bauman et al. |
| 2009/0043334 A1 | 2/2009 | Bauman et al. |
| 2009/0078739 A1 | 3/2009 | Viola |
| 2009/0095791 A1 | 4/2009 | Eskaros et al. |
| 2009/0095792 A1 | 4/2009 | Bettuchi |
| 2009/0120994 A1 | 5/2009 | Murray et al. |
| 2009/0134200 A1 | 5/2009 | Tarinelli et al. |
| 2009/0206125 A1 | 8/2009 | Huitema et al. |
| 2009/0206126 A1 | 8/2009 | Huitema et al. |
| 2009/0206139 A1 | 8/2009 | Hall et al. |
| 2009/0206141 A1* | 8/2009 | Huitema .......... A61B 17/07207 227/176.1 |
| 2009/0206142 A1 | 8/2009 | Huitema et al. |
| 2009/0206143 A1 | 8/2009 | Huitema et al. |
| 2009/0218384 A1 | 9/2009 | Aranyi |
| 2009/0277944 A9* | 11/2009 | Dalessandro .... A61B 17/07207 227/154 |
| 2009/0277947 A1 | 11/2009 | Viola |
| 2009/0287230 A1 | 11/2009 | D'Agostino et al. |
| 2010/0012704 A1 | 1/2010 | Tarinelli Racenet et al. |
| 2010/0065606 A1 | 3/2010 | Stopek |
| 2010/0065607 A1 | 3/2010 | Orban, III et al. |
| 2010/0072254 A1 | 3/2010 | Aranyi et al. |
| 2010/0147921 A1 | 6/2010 | Olson |
| 2010/0147922 A1 | 6/2010 | Olson |
| 2010/0147923 A1 | 6/2010 | D'Agostino et al. |
| 2010/0234861 A1* | 9/2010 | Oray ................ A61B 17/07207 606/151 |
| 2010/0243706 A1* | 9/2010 | Cohen ............. A61B 17/07207 227/176.1 |
| 2010/0243707 A1 | 9/2010 | Olson et al. |
| 2010/0243708 A1 | 9/2010 | Aranyi et al. |
| 2010/0243711 A1 | 9/2010 | Olson et al. |
| 2010/0249805 A1 | 9/2010 | Olson et al. |
| 2010/0264195 A1 | 10/2010 | Bettuchi |
| 2010/0282815 A1 | 11/2010 | Bettuchi et al. |
| 2011/0024476 A1 | 2/2011 | Bettuchi et al. |
| 2011/0024481 A1 | 2/2011 | Bettuchi et al. |
| 2011/0036894 A1 | 2/2011 | Bettuchi |
| 2011/0042442 A1 | 2/2011 | Viola et al. |
| 2011/0046650 A1 | 2/2011 | Bettuchi |

(56) References Cited

U.S. PATENT DOCUMENTS

| | | |
|---|---|---|
| 2011/0057016 A1 | 3/2011 | Bettuchi |
| 2011/0233259 A1* | 9/2011 | Olson .................. A61B 17/072 227/176.1 |
| 2012/0145767 A1* | 6/2012 | Shah ................ A61B 17/07207 227/180.1 |

FOREIGN PATENT DOCUMENTS

| | | | |
|---|---|---|---|
| EP | 0594148 | 4/1994 | |
| EP | 0327022 | 4/1995 | |
| EP | 0667119 | 8/1995 | |
| EP | 1520525 | 4/2005 | |
| EP | 1759640 | 3/2007 | |
| EP | 2005895 | 12/2008 | |
| EP | 2236097 A1 * | 6/2010 | ........... A61B 17/072 |
| EP | 2236097 A1 | 10/2010 | |
| EP | 2462880 | 6/2012 | |
| JP | 06327683 | 11/1994 | |
| WO | WO 90/05489 | 5/1990 | |
| WO | WO 97/13463 | 4/1997 | |
| WO | WO 98/17180 | 4/1998 | |
| WO | WO 99/45849 | 9/1999 | |
| WO | WO 00/56376 | 9/2000 | |
| WO | WO 01/62158 | 8/2001 | |
| WO | WO 01/62162 | 8/2001 | |
| WO | WO 02/30297 | 4/2002 | |
| WO | WO 03/082126 | 10/2003 | |
| WO | WO 03/088844 | 10/2003 | |
| WO | WO 03/088845 | 10/2003 | |
| WO | WO 03/094743 | 11/2003 | |
| WO | WO 03/094746 | 11/2003 | |
| WO | WO 03/105698 | 12/2003 | |
| WO | WO 2006/023578 | 3/2006 | |
| WO | WO 2006/044490 | 4/2006 | |
| WO | WO 2006/083748 | 8/2006 | |
| WO | WO 2008/057281 | 5/2008 | |
| WO | WO 2008/109125 | 9/2008 | |

OTHER PUBLICATIONS

International Search Report corresponding to European Application No. EP 06 00 4598, completed on Jun. 22, 2006; 2 pages.
International Search Report corresponding to European Application No. EP 06 01 6962, completed on Jan. 3, 2007 and mailed on Jan. 11, 2007; 10 pages.
International Search Report corresponding to International Application No. PCT/US2005/036740, completed on Feb. 20, 2007 and mailed on Mar. 23, 2007; 3 pages.
International Search Report corresponding to International Application No. PCT/US2007/022713, completed on Apr. 21, 2008; 3 pages.
International Search Report corresponding to International Application No. PCT/US2005/037253, completed on Apr. 29, 2008 and mailed on May 28, 2008; 3 pages.
International Search Report corresponding to International Application No. PCT/US2008/002981, completed on Jun. 9, 2008 and mailed on Jun. 26, 2008; 4 pages.
International Search Report corresponding to European Application No. EP 08 25 1779, completed on Jul. 14, 2008 and mailed on Jul. 23, 2008; 5 pages.
International Search Report corresponding to European Application No. EP 08 25 1989.3, completed on Mar. 11, 2010 and mailed on Mar. 24, 2010; 3 pages.
International Search Report corresponding to European Application No. EP 05 80 4382.9, completed on Oct. 5, 2010 and mailed on Oct. 12, 2010; 3 pages.
International Search Report corresponding to European Application No. EP 10 25 1437.9, completed on Nov. 22, 2010 and mailed on Dec. 16, 2010; 3 pages.
International Search Report corresponding to European Application No. EP 09 25 2897.5, completed on Feb. 7, 2011 and mailed on Feb. 15, 2011; 3 pages.
International Search Report corresponding to European Application No. EP 05 80 9831.0-1269, completed on May 4, 2012; 10 pages.
European Office Action corresponding to EP 13196822.4 dated May 18, 2015; 4 pp.
Extended European Search Report corresponding to EP 13 19 6822.4, completed Mar. 14, 2014 and mailed Mar. 25, 2014; (8 pp).
European Office Action corresponding to counterpart International Application No. EP 13 196 822.4, dated Sep. 23, 2015; (4 pp.).
European Office Action corresponding to counterpart Int'l, Appln. No. EP 15 16 6762.3 dated Jun. 7, 2016.

* cited by examiner

SURGICAL INSTRUMENT WITH PRESSURE DISTRIBUTION DEVICE

BACKGROUND

1. Technical Field

The present disclosure relates to medical instruments and the use thereof. More particularly, the present disclosure is directed to medical staplers and pressure distribution during a clamping and/or stapling procedure.

2. Background of Related Art

Generally, surgical fastener applying instruments grasp or clamp tissue between opposing jaw structures and join the tissue by means of surgical fasteners. In some such instruments, a knife is provided to cut the tissue which has been joined by the fasteners. The fasteners are typically in the form of surgical staples, although other surgical fasteners may also be utilized, such as, for example, clips or two part polymeric surgical fasteners.

Certain surgical fastener applying instruments include two elongated jaw members which are used to capture or clamp tissue therebetween. Typically, one of the jaw members carries a cartridge assembly which houses a plurality of staples arranged in at least two lateral rows, while the other jaw member includes an anvil which defines a surface for forming the staple legs as the staples are driven from the cartridge assembly. Where two part fasteners are used, the jaw member which includes the anvil carries a mating part of the two part fastener, e.g. the receiver. Generally, the staple formation process is effected by the interaction between one or more longitudinally moving camming members and a series of individual staple pushers. As the camming members travel longitudinally through the cartridge carrying jaw member, the individual staple pushers are urged upwardly into a backspan of the staples supported within the cartridge assembly to sequentially eject the staples from the cartridge assembly. A knife may be provided to travel with the camming members between the staple rows to cut the tissue between the rows of formed staples.

Pinching may occur at the site of clamped tissue along the periphery of the jaw members due to a very localized high pressure gradient between the clamped tissue and the tissue lying outside the jaws. This pinching may affect the quality of the procedure. Solutions to these issues are described hereinbelow.

SUMMARY

In accordance with at least one aspect of the present disclosure, a surgical apparatus includes an anvil jaw configured to form at least one surgical staple, a cartridge jaw configured to deploy one or more surgical staples against the anvil jaw, and a pressure distribution device attached to at least one of the anvil jaw and the cartridge jaw, wherein the pressure distribution device is configured to distribute a clamping pressure to a target tissue during a clamping and a stapling of the target tissue.

Each pressure distribution device may include at least one flap extending from a side of a respective anvil jaw and cartridge jaw.

Each pressure distribution device may be made of a shape memory material, or can be reinforced with a shape memory material.

Each pressure distribution device may be furled up in a retracted state against at least one of the anvil jaw and the cartridge jaw such that the apparatus has a low profile.

Each of the anvil jaw and the cartridge jaw may comprise at least one pressure distribution device attached to a surface thereof.

Each pressure distribution device may be furled up in a retracted state such that the apparatus has a low profile.

Each pressure distribution device may be substantially U-shaped and extends beyond a distal end of the respective anvil jaw and cartridge jaw.

At least one pressure distribution device may include an inflatable bladder that is deflated in a retracted state and inflated in an extended state.

At least one pressure distribution device may further include a deployment member that holds the at least one flap in a refracted state, and is configured to allow the at least one flap to move to an extended state.

The deployment member may be a tubular member slidably disposed on the apparatus, configured to slide between a distal position surrounding the at least one flap and holding the at least one flap in the retracted state, and a proximal position to release the at least one flap and allow the at least one flap to move to an extended state.

The deployment member may include at least one or more ties that bind the at least one flap in the retracted state.

In accordance with still yet another aspect of the present disclosure, a method includes providing a surgical apparatus including an anvil jaw, a cartridge jaw configured to deploy one or more surgical staples into the anvil jaw, and a pressure distribution device attached to at least one of the anvil jaw and the cartridge jaw, wherein the pressure distribution device is configured to distribute pressure to a target tissue during clamping and stapling of a target tissue, and deploying the pressure distribution device before clamping and stapling a target tissue.

The deploying of the pressure distribution device may be performed after clamping but before stapling.

Each pressure distribution device may be furled up in a retracted state against at least one of the anvil jaw and the cartridge jaw such that the apparatus has a low profile, the method further comprising passing the surgical apparatus through a cannula in the retracted state.

The method may further include the step of unfurling the pressure distribution device from the retracted state to a deployed state after passing the pressure distribution device through a cannula.

The method may further include the step of clamping target tissue after unfurling the pressure distribution device.

The method may further include the step of stapling target tissue after clamping target tissue.

The method may further include the step of unclamping target tissue after stapling.

The method may further include the step of furling the pressure distribution device back into the retracted state after unclamping target tissue.

BRIEF DESCRIPTION OF THE DRAWINGS

The above and other aspects, features, and advantages of the present disclosure will become more apparent in light of the following detailed description when taken in conjunction with the accompanying drawings in which.

DETAILED DESCRIPTION

Figure 1:
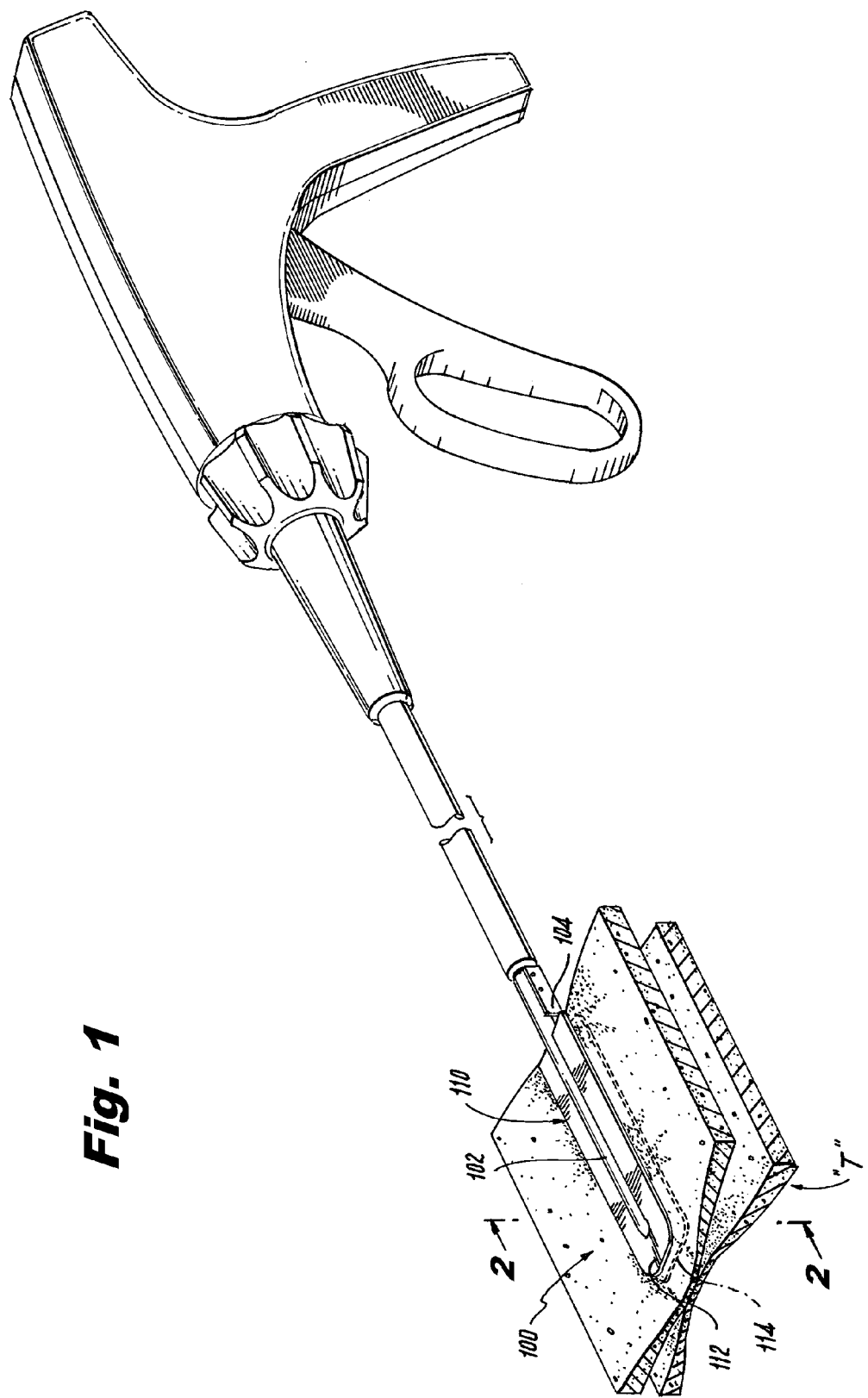
FIG. 1 is a perspective view of at least one embodiment of a surgical instrument in accordance with the present disclosure.

Like reference numerals may refer to similar or identical elements throughout the description of the figures. As shown in the drawings and described throughout the following description, as is traditional when referring to relative positioning on a surgical instrument, the term "proximal" refers to the end of the apparatus that is closer to the user and the term "distal" refers to the end of the apparatus that is farther away from the user. The term "clinician" refers to any medical professional (e.g., doctor, surgeon, nurse, or the like) performing a medical procedure involving the use of embodiments described herein.

Particular embodiments of the present disclosure are described hereinbelow with reference to the accompanying drawings; however, the disclosed embodiments are merely examples of the disclosure and may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure.

In accordance with at least one aspect of the present disclosure, a surgical instrument is described herein. The surgical instrument may be a tissue stapling apparatus or a tissue clamping apparatus, such as, for example, an end effector, disposable loading unit (DLU), single use loading unit (SULU), multi use loading unit (MULU), etc. The apparatus can include removable and replaceable parts, such as a reload or loading unit that includes the anvil and cartridge assembly (SULU). The cartridge assembly may be removable and replaceable in an instrument that has jaws that are intended to be reused during the same procedure, or removable and replaceable in a SULU.

A tissue stapling apparatus, as shown in FIGS. 1-9B, may generally include an anvil jaw supporting an anvil and a cartridge jaw supporting a cartridge assembly, wherein the anvil and cartridge assembly cooperate with one another to clamp the target tissue, and to deploy one or more surgical staples into target tissue and form the one or more surgical staples.

Each embodiment shown in the figures further includes at least one embodiment of a pressure distribution device or attachment in accordance with the present disclosure. Generally, the at least one pressure distribution device or attachment may be permanently or selectively attached to one or both of the anvil jaw and the cartridge jaw.

The pressure distribution device or attachment may be made into any suitable shape to contact a target tissue and reduce the pressure associated with a clamping of the target tissue by the surgical instrument. Specific embodiments of the pressure distribution device or attachment are described in more detail below.

The apparatus can include a manually operated and manually powered handle portion, a motorized powered handle portion with an internal or external power source, or other interface for actuating the end effector.

Figure 2:
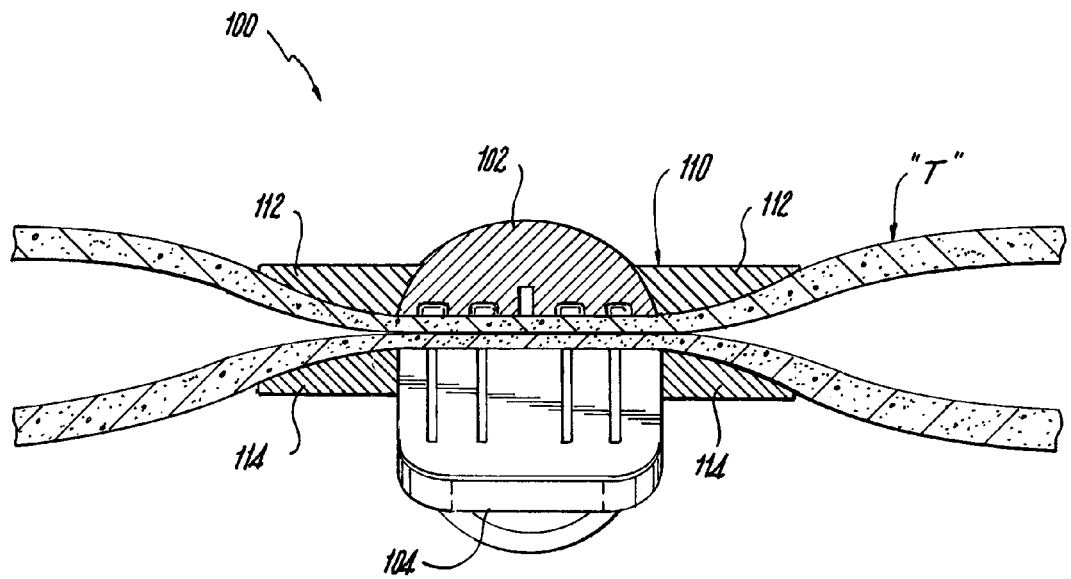
FIG. 2 is a front, elevational view, partially in section, of the surgical instrument of FIG. 1.
Figure 3:
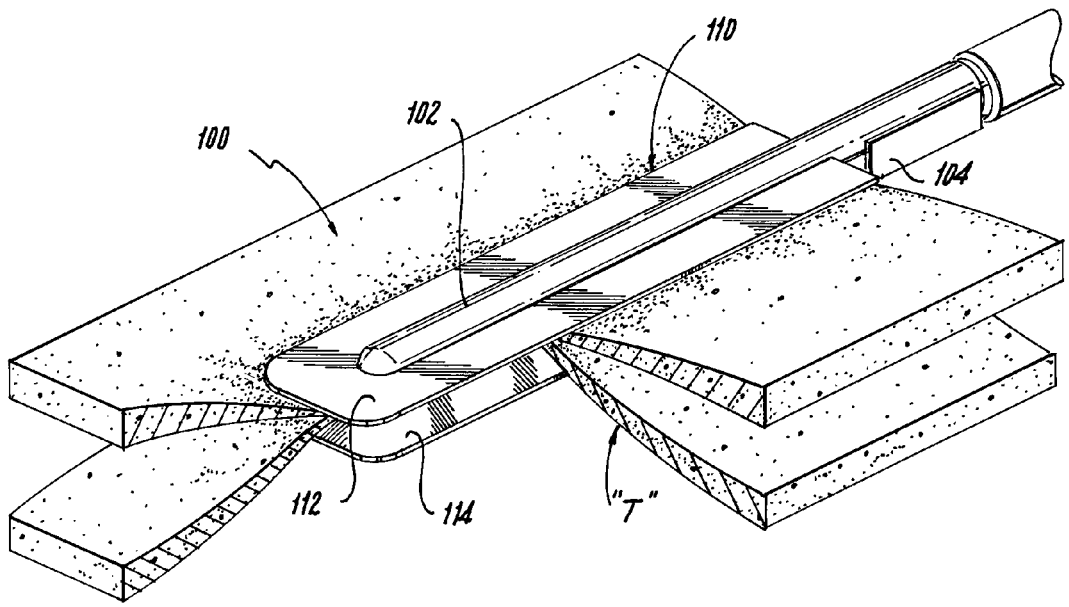
FIG. 3 is a perspective view of the surgical instrument of FIG. 1.

Referring specifically to FIGS. 1-3, an end effector 100, in accordance with an embodiment of the present disclosure, for use with a surgical instrument is shown. End effector 100 includes an anvil jaw or portion 102, a cartridge jaw or portion 104, and a pressure distribution device or attachment 110 is shown. Reference may be made to U.S. Patent Publication No. 2009/0314821, filed on Aug. 31, 2009, the entire content of which is incorporated herein, for a detailed discussion of the construction and operation of an exemplary surgical instrument.

As depicted, the end effector 100 is clamped down on the target tissue "T" with the pressure distribution device or attachment 110 shown in an extended or deployed state. The pressure distribution device or attachment 110 is configured to distribute a clamping pressure to the target tissue "T" during clamping and stapling of the target tissue "T".

The pressure distribution device or attachment 110 includes at least one anvil flap 112 and/or at least one cartridge flap 114 extending from a side of the anvil jaw 102 or the cartridge jaw 104, respectively.

As shown in FIGS. 1-3, the flaps 112, 114 may be substantially U-shaped in an axial direction such that the flaps 112, 114 extend from a proximal portion and wrap around a distal end of respective anvil jaw 102 and cartridge jaw 104.

In operation, when anvil jaw 102 and cartridge jaw 104 are clamped onto target tissue "T", flaps 112, 114 of pressure distribution device or attachment 110 extend outwardly therefrom and across the target tissue "T". In so doing, flaps 112, 114 increase a surface area of the tissue contacting surfaces of anvil jaw 102 and cartridge jaw 104. By increasing the surface area of the tissue contacting surfaces of anvil jaw 102 and cartridge jaw 104, pressure distribution device 110 distributes a clamping load away from the hard edges of anvil jaw 102 and cartridge jaw 104, wherein the clamping load gradually transitions.

Flaps 112, 114 may be sized to any desired width or length on jaws 102 and 104. Flaps 112, 114 do not have to be of identical size or shape. For example, flap 112 may be wider, thicker, and/or longer than flap 114 and vice versa.

Each flap 112, 114 of pressure distribution device or attachment 110 may be made of a high durometer rubber, shape memory material, a foam, a gel, a plastic, a spring loaded plastic, or any other suitable material.

Figure 4:
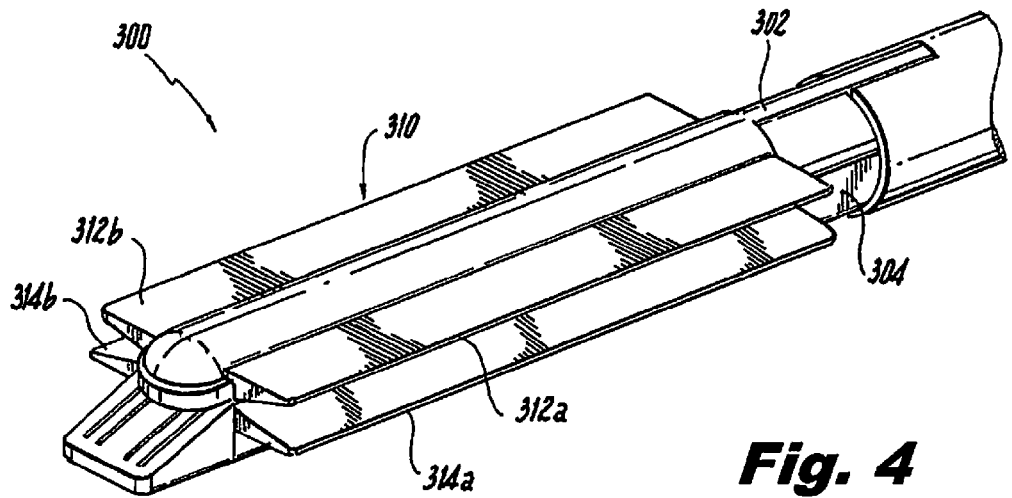
FIG. 4 is a schematic, perspective view of another embodiment of a surgical instrument in accordance with the present disclosure.

Referring to FIG. 4, another embodiment of an end effector 300 including a pressure distribution device or attachment 310 is shown. The pressure distribution device or attachment 310 includes a first anvil flap 312a and a second anvil flap 312b attached to opposed lateral sides of the anvil jaw 302. Pressure distribution device or attachment 310 also includes a first cartridge flap 314a and a second cartridge flap 314b attached to opposed lateral sides of the cartridge jaw 304.

Figure 5A:
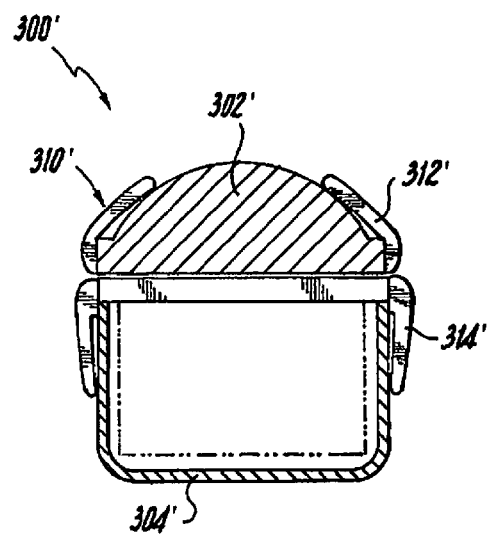
FIG. 5A is a front, elevational view, partially in section, of at least one embodiment of a surgical instrument in accordance with the present disclosure, shown in a retracted state.
Figure 5B:
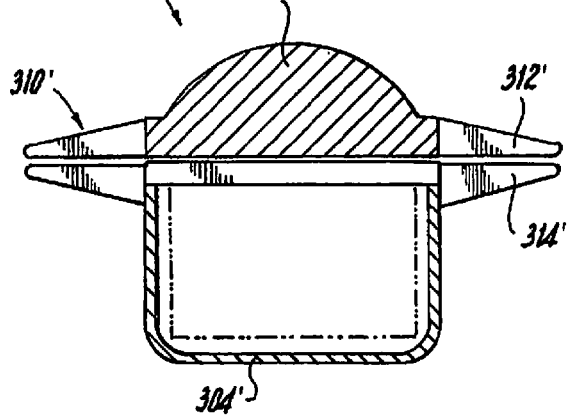
FIG. 5B is a front, elevational view, partially in section, of the surgical instrument of FIG. 5A, shown in an extended or deployed state.

With reference to FIGS. 5A and 5B, an end effector 300' is shown illustrating an embodiment of a pressure distribution device or attachment 310' in a refracted state and an extended or deployed state, respectively. As shown in FIG. 5A, the flaps 312', 314' may be furled up against the anvil jaw 302' and the cartridge jaw 304', respectively, such that the transverse cross-sectional profile of the end effector 300', has a low profile, wherein the end effector 300' is capable of being inserted through a cannula (not shown) to reach a target surgical site. In FIG. 5B, the flaps 312', 314' are unfurled such that the flaps 312', 314' extend laterally outward from the anvil jaw 302' and the cartridge jaw 304', respectively, to increase the effective surface area of each jaw, as described above. The flaps may be temporarily attached to the jaws initially. Yes, they can be temporarily attached by means or adhesive or snap features.

Figure 6A:
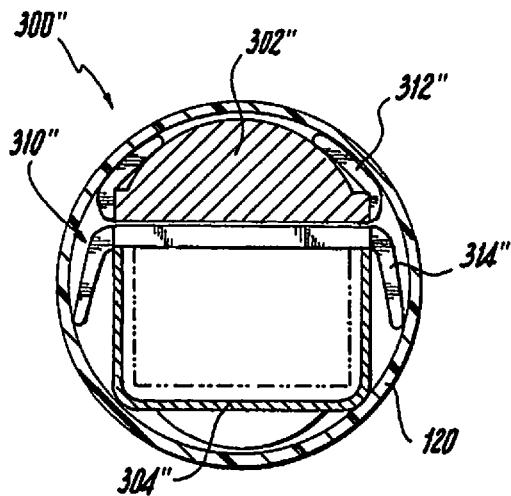
FIG. 6A is a front, elevational view, partially in section, of another embodiment of a surgical instrument in accordance with the present disclosure, shown in a retracted state.
Figure 6B:
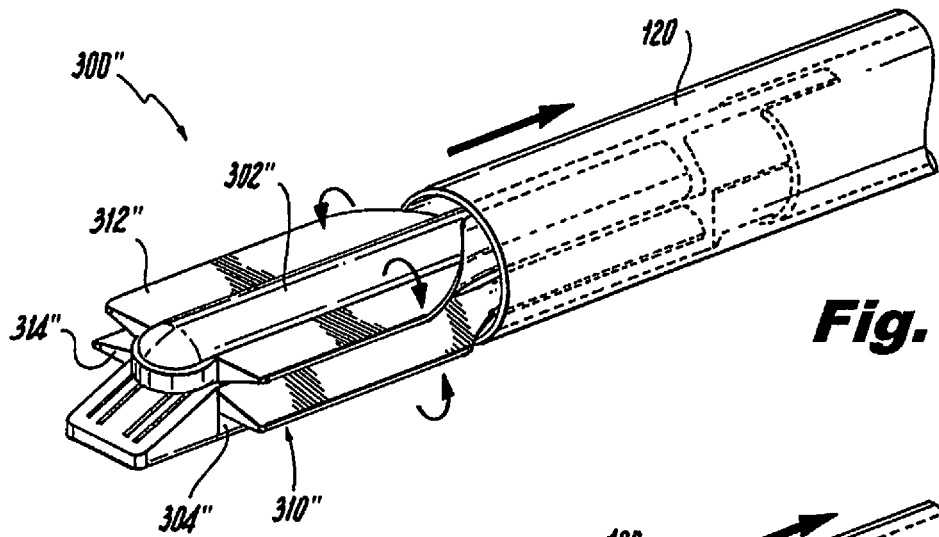
FIG. 6B is a perspective view of the surgical instrument of FIG. 6A, shown in a retracted state.
Figure 6C:
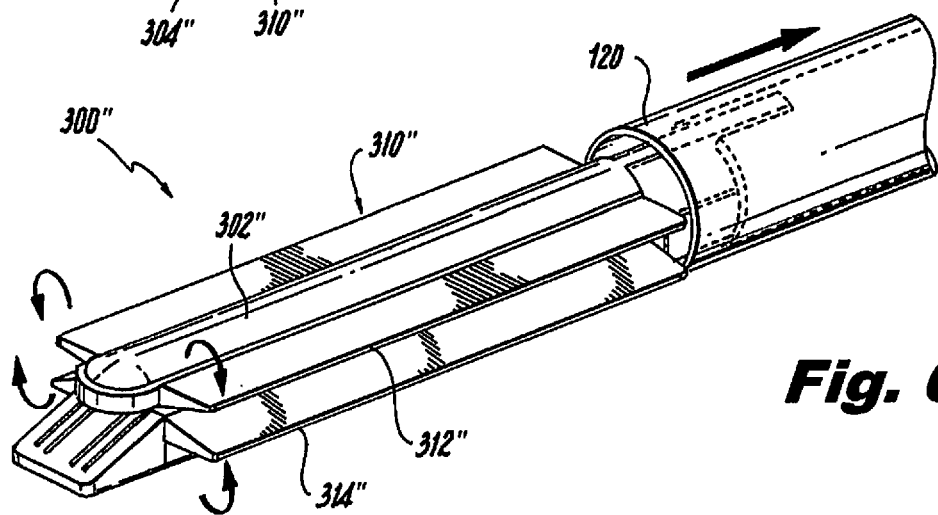
FIG. 6C is a perspective view of the surgical instrument of FIG. 6A, shown in a deployed or extended state.

Referring now to FIGS. 6A-6C, a deployment device/tube 120 may be provided for use in conjunction with an end effector 300" and a pressure distribution device or attachment 310". Deployment tube 120 may be a tubular member slidably connected to or disposed about end effector 300" such that the deployment tube 120 may selectively cover and expose the flaps 312", 314" of the anvil jaw 302" and the cartridge jaw 304", respectively.

As seen in FIGS. 6A and 6B, pressure distribution device or attachment 310" is shown in a retracted state having the deployment tube 120 disposed over the flaps 312", 314", whereby deployment tube 120 facilitates passage of end effector 300" through a cannula (not shown). FIG. 6C shows the deployment tube 120 in a withdrawn or retracted condition exposing the flaps 312", 314" such that the flaps 312", 314" are free to unfurl into the extended or deployed state, either manually or due to restoring force acting on the flaps 312", 314". The tube could be integral to the instrument working shaft. The tube may also take the form of a cap that is pulled off manually by using a set of graspers after having been inserted through the cannula.

Figure 7A:
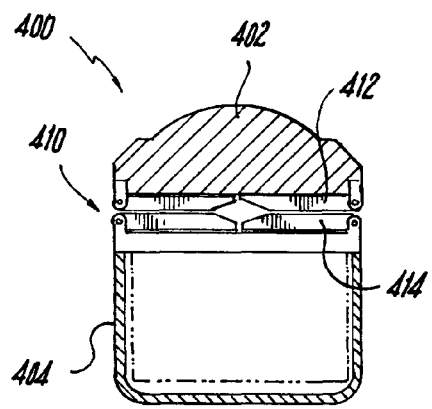
FIG. 7A is a front, elevational view, partially in section, of another embodiment of a surgical instrument in accordance with the present disclosure, shown in a retracted state.
Figure 7B:
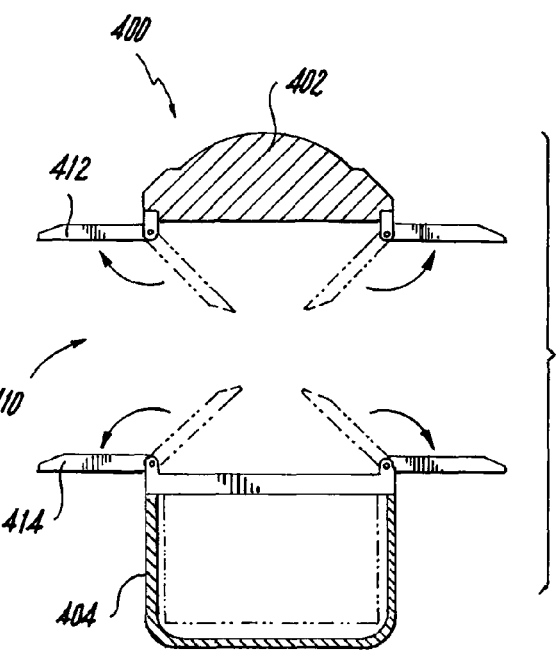
FIG. 7B is a front, elevational view, partially in section, of the surgical instrument of FIG. 7A, shown in a deployed or extended state.

Referring now to FIGS. 7A and 7B, a pressure distribution device or attachment 410 in accordance with another embodiment of the disclosure, associated with end effector 400, is shown in a retracted state and an extended or deployed state, respectively. As shown in FIG. 7A, the flaps 412, 414 may be furled or folded to overlie the tissue contacting surfaces and are sandwiched between anvil jaw 402 and the cartridge jaw 404 such that the end effector 400 is capable of being inserted through a cannula (not shown) to reach a surgical site. In FIG. 7B, the flaps 412, 414 are unfurled after separating the anvil jaw 402 and the cartridge jaw 404 such that the flaps 412, 414 extend laterally outward from the anvil jaw 402 and the cartridge jaw 404 to increase the effective surface area of each jaw.

It is important to note that while the flaps 412, 414 are shown as rigid linkages attached to the anvil jaw 402 and cartridge jaw 404 via a mechanical hinge, flaps 412, 414 may be of any suitable material and attached as described herein or otherwise.

Figure 8A:
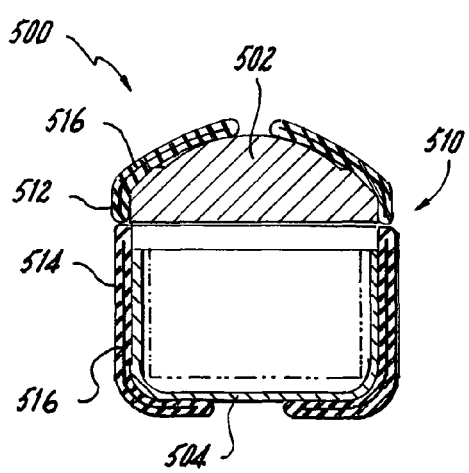
FIG. 8A is a front, elevational view of another embodiment of a surgical instrument in accordance with the present disclosure, shown in a retracted state.
Figure 8B:
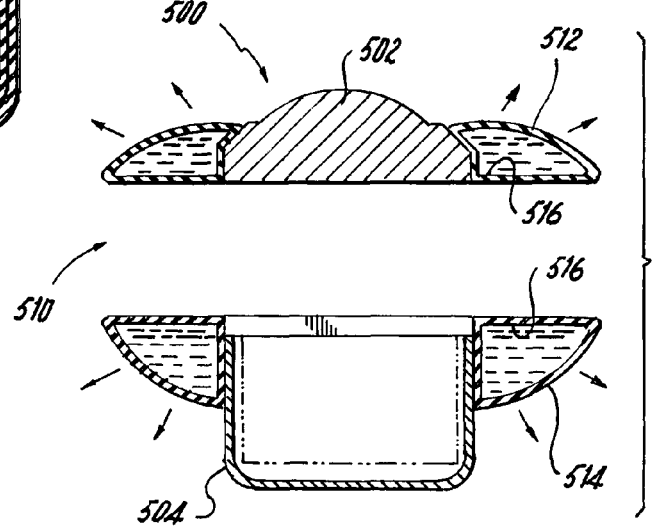
FIG. 8B is a front, elevational view, partially in section, of the surgical instrument of FIG. 8A, shown in a deployed or inflated state.

Referring now to FIGS. 8A and 8B, a pressure distribution device or attachment 510 in accordance with another embodiment of the present disclosure, associated with end effector 500, is shown in a retracted state and an extended or deployed state, respectively. Pressure distribution device or attachment 510 includes at least one inflatable bladder 516 disposed in at least one flap 512, 514 that is deflated in a retracted state and inflated in an extended or deployed state. The inflatable bladders 516 may be connected to a pressurized fluid supply (not shown) and inflated/deflated as need or desired. The flaps may be made from an elastic membrane so that they extend and retract. They can be made of a plastic or elastomeric material to provide flexibility. The deflection of the flaps would be controlled in the design by means of thickness. Closer to the jaws, the flaps would be thicker to minimize the amount of deflection in the flap. The flaps would progressively get thinner further away from the jaws to allow for more deflection.

As shown in FIG. 8A, the flaps 512, 514 may be deflated and retracted up against the anvil jaw 502 and the cartridge jaw 504, respectively, such that the profile of the end effector 500 allows insertion through a cannula (not shown) to reach a surgical site. In FIG. 8B, the bladders 516 are pressurized with fluid (e.g., air, CO2, saline, etc.) and flaps 512, 514 are inflated such that the flaps 512, 514 extend laterally outward from the anvil jaw 502 and the cartridge jaw 504, respectively, to increase the effective surface area of each jaw. Flaps 512, 514 may also be deflated for removal or withdrawal of the end effector 500 through the cannula (not shown). In any of the embodiments disclosed herein, the pressure distribution device or attachment can include one or more inflatable and/or fillable flap extending away from the jaw or jaws in one or more directions.

Figure 9A:
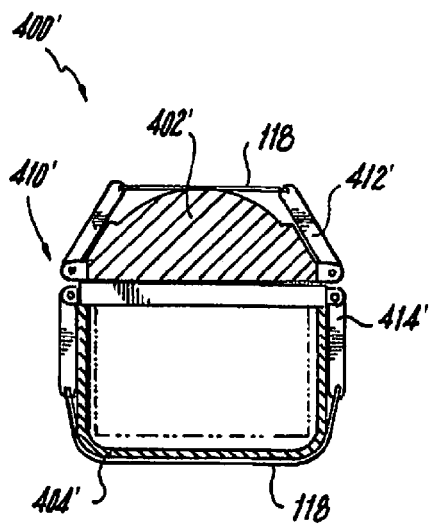
FIG. 9A is a front, elevational view, partially in section, of another embodiment of a surgical instrument in accordance with the present disclosure, shown in a retracted state.
Figure 9B:
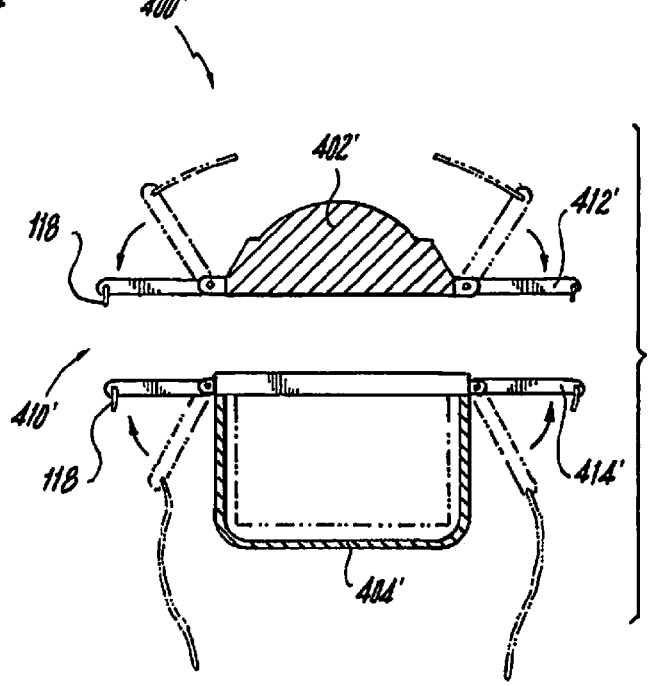
FIG. 9B is a front, elevational view, partially in section, of the surgical instrument of FIG. 9A, shown in a deployed or extended state.

Referring now to FIGS. 9A and 9B, an end effector 400' is shown illustrating a pressure distribution device or attachment 410' in a retracted state and an extended or deployed state, respectively. Pressure distribution device or attachment 410' includes at least one deployment member 118, according to an embodiment of the present disclosure that holds the flaps 412', 414' in the retracted state. For example, deployment members 118 may be one or more ties or tethers that bind the flaps 412', 414' to the retracted state. Other means for temporarily retaining the flaps are adhesives, snap features, ties, straps, etc.

The deployment members 118 are configured to selectively separate from flaps 412', 414' to allow the flaps 412', 414' to unfurl to the extended or deployed state. For example, deployment members 118 may be manually cut, snapped, or untied. In other embodiments, the deployment members 118 may be made of a dissolvable material such that the introduction of a fluid (e.g., saline or water) will dissolve the deployment members 118 and allow the flaps 412', 414' to unfurl to the extended or deployed state.

As shown in FIG. 9A, the flaps 412', 414' may be folded or furled up against the anvil jaw 402' and the cartridge jaw 404' such that the profile of the end effector 400' allows insertion through a cannula (not shown) to reach a target surgical site. In FIG. 9B, the deployment members 118 are snapped, and flaps 412', 414' are unfurled such that the flaps 412', 414' extend laterally outward from the anvil jaw 402' and the cartridge jaw 404' to increase the effective surface area of each jaw. As with other embodiments, flaps 412', 414' may be furled or folded back into a retracted state for removal of the end effector 400' through the cannula (not shown). The flaps, in any of the embodiments disclosed herein, can extend in one or more directions, from one or more sides of the jaw or jaws.

It is important to note that while the flaps 412', 414' are shown as rigid linkages attached to the anvil jaw 402' and the cartridge jaw 404' via a mechanical hinge, flaps 412', 414' may be of any suitable material and attached as described herein or otherwise.

In at least some embodiments, the above described pressure distribution devices or attachments may be combined in any suitable manner. For example, a pressure distribution device or attachment may include at least one of a flap having an inflatable bladder, a flap having a tie that binds the flap into the refracted position, and a tubular member that prevents the flap from moving to the extended or deployed position. Many other combinations are contemplated, but are not expressly disclosed herein for the sake of brevity.

In at least one aspect of the present disclosure, a method includes providing a surgical instrument and/or end effector having a pressure distribution device or attachment as described herein, and deploying the pressure distribution device or attachment before clamping and stapling a target tissue.

Sensors may be used, in any of the embodiments disclosed herein. A pressure sensor can be incorporated in or on the pressure distribution device. An inflatable device can include a sensor for the pressure of the fluid or other medium inside the pressure distribution device. The flaps may be constructed of or include thin film sensors (strain gauges, capacitive sensors, etc.) that will provide feedback to the handle and ultimately the user with regards to tissue thickness and the pressure being applied to the tissue by the flaps. This electrical data may be communicated to the handle by means of a hardwired connection as well as a wireless data communication.

It should be understood that the foregoing description is only illustrative of the present disclosure. Various alternatives and modifications can be devised by those skilled in the art without departing from the disclosure. Accordingly, the present disclosure is intended to embrace all such alternatives, modifications and variances. The embodiments described with reference to the attached drawing figures are presented only to demonstrate certain examples of the disclosure. Other elements, steps, methods and techniques that are insubstantially different from those described above and/or in the appended claims are also intended to be within the scope of the disclosure.

What is claimed is:

1. A surgical apparatus, comprising:
    an anvil jaw configured to form at least one surgical staple;
    a cartridge jaw configured to deploy one or more surgical staples against the anvil jaw; and
    a pressure distribution device including at least one flap attached to the anvil jaw or the cartridge jaw by a mechanical hinge, the at least one flap being non-inflatable and movable between a retracted state in which the at least one flap is furled against the anvil jaw or the cartridge jaw and an extended state in which the at least one flap extends outwardly from the anvil jaw or the cartridge jaw to distribute a clamping pressure to a target tissue during a clamping and a stapling of the target tissue.

2. The apparatus of claim 1, wherein the pressure distribution device is made of a shape memory material.

3. The apparatus of claim 1, wherein the at least one flap includes at least one anvil flap attached to the anvil jaw and at least one cartridge flap attached to the cartridge jaw.

4. The apparatus of claim 1, wherein the at least one flap includes an anvil flap attached to the anvil jaw and a cartridge flap attached to the cartridge jaw, wherein each of the anvil and cartridge flaps of the pressure distribution device is substantially U-shaped and extends beyond a distal end of the respective anvil jaw and cartridge jaw.

5. The apparatus of claim 1, wherein the at least one flap of the pressure distribution device includes at least two anvil flaps or two cartridge flaps extending from opposed lateral sides of the anvil jaw or the cartridge jaw.

6. The apparatus of claim 1, wherein the at least one flap of the pressure distribution device overlies an outer surface of the anvil jaw or the cartridge jaw when in the retracted state.

7. The apparatus of claim 1, wherein the at least one flap of the pressure distribution device overlies a tissue contacting surface of the anvil jaw or the cartridge jaw when in the retracted state.

8. A surgical apparatus, comprising:
    an anvil jaw configured to form at least one surgical staple;
    a cartridge jaw configured to deploy one or more surgical staples against the anvil jaw;
    a pressure distribution device including at least one flap attached to the anvil jaw or the cartridge jaw, the at least one flap being non-inflatable and movable between a retracted state in which the at least one flap is furled against the anvil jaw or the cartridge jaw and an extended state in which the at least one flap extends outwardly from the anvil jaw or the cartridge jaw to distribute a clamping pressure to a target tissue during a clamping and a stapling of the target tissue; and
    a deployment member that holds the at least one flap in the retracted state, and is configured to allow the at least one flap to move to the extended state, and wherein the deployment member is a tubular member slidably disposed on the apparatus, and wherein the deployment member is configured to slide between a distal position surrounding the at least one flap and holding the at least one flap in the retracted state, and a proximal position to release the at least one flap and allow the at least one flap to move to an extended state.

9. The apparatus of claim 8, wherein the deployment member includes at least one or more ties that bind the at least one flap in the retracted state.

* * * * *